(12) United States Patent
Schuetzle et al.

(10) Patent No.: US 12,104,125 B2
(45) Date of Patent: *Oct. 1, 2024

(54) EFFICIENT 2-STEP PROCESS FOR THE DIRECT PRODUCTION OF LIQUID FUELS FROM CARBON DIOXIDE AND HYDROGEN

(71) Applicant: INFINIUM TECHNOLOGY, LLC, Sacramento, CA (US)

(72) Inventors: Robert Schuetzle, Sacramento, CA (US); Dennis Schuetzle, Grass Valley, CA (US); Orion Hanbury, Sacramento, CA (US)

(73) Assignee: Infinium Technology, LLC, Sacramento, CA (US)

( * ) Notice: Subject to any disclaimer, the term of this patent is extended or adjusted under 35 U.S.C. 154(b) by 834 days.

This patent is subject to a terminal disclaimer.

(21) Appl. No.: 17/300,009

(22) Filed: Feb. 5, 2021

(65) Prior Publication Data

US 2022/0251455 A1 Aug. 11, 2022

(51) Int. Cl.
*C10G 2/00* (2006.01)
*B01J 21/00* (2006.01)
(Continued)

(52) U.S. Cl.
CPC ............. *C10G 2/50* (2013.01); *B01J 21/005* (2013.01); *B01J 21/04* (2013.01); *B01J 21/08* (2013.01);
(Continued)

(58) Field of Classification Search
CPC ... C07C 1/0435; C07C 2523/78; C01B 32/50; C25B 1/04
See application file for complete search history.

(56) References Cited

U.S. PATENT DOCUMENTS 4,990,491 A 2/1991 Wagner et al.
6,402,989 B1 6/2002 Gaffney et al.
(Continued)

FOREIGN PATENT DOCUMENTS

AU 2015/203898 B2 8/2015
GB 2279583 1/1995

OTHER PUBLICATIONS

Allam, R., et al., "High efficiency and low cost of electricity generation from fossil fuels while eliminating . . . " Energy Procedia 37, 1135-1149 (2013).
(Continued)

*Primary Examiner* — Jafar F Parsa
(74) *Attorney, Agent, or Firm* — McKinney Law Group APC; Jeffrey A. McKinney

(57) ABSTRACT

Embodiments of the present invention relate to two improved catalysts and associated processes that directly convert carbon dioxide and hydrogen to liquid fuels. A catalytic system comprises two catalysts in series that are operated in tandem to directly produce synthetic liquid fuels. The carbon conversion efficiency for $CO_2$ to liquid fuels is greater than 45%. The fuel is distilled into a premium diesel fuels (approximately 70 volume %) and naphtha (approximately 30 volume %) which are used directly as "drop-in" fuels without requiring any further processing. Any light hydrocarbons that are present with the carbon dioxide are also converted directly to fuels. This process is directly applicable to the conversion of $CO_2$ collected from ethanol plants, cement plants, power plants, biogas, carbon dioxide/hydrocarbon mixtures from secondary oil recovery, and other carbon dioxide/hydrocarbon streams. The catalyst system is durable, efficient and maintains a relatively constant level of fuel productivity over long periods of time without requiring re-activation or replacement.

8 Claims, 2 Drawing Sheets

Process Flow Diagram for the Improved Catalysts and Processes used for the Direct Production of Liquid Fuels from $CO_2$ and Green $H_2$

(51) Int. Cl.

| | | |
|---|---|---|
| *B01J 21/04* | (2006.01) | |
| *B01J 21/08* | (2006.01) | |
| *B01J 21/12* | (2006.01) | |
| *B01J 23/78* | (2006.01) | |
| *B01J 23/89* | (2006.01) | |
| *B01J 35/00* | (2024.01) | |
| *B01J 35/30* | (2024.01) | |
| *C07C 1/12* | (2006.01) | |
| *C25B 1/04* | (2021.01) | |

(52) U.S. Cl.
CPC ............. *B01J 21/12* (2013.01); *B01J 23/78* (2013.01); *B01J 23/8946* (2013.01); *B01J 23/8986* (2013.01); *B01J 35/00* (2013.01); *B01J 35/30* (2024.01); *C07C 1/12* (2013.01); *C10G 2/30* (2013.01); *C25B 1/04* (2013.01); *C10G 2300/42* (2013.01)

(56) References Cited

U.S. PATENT DOCUMENTS

| | | |
|---|---|---|
| 6,432,665 B1 | 8/2002 | Okado et al. |
| 6,946,114 B2 | 9/2005 | Allison et al. |
| 7,432,222 B2 | 10/2008 | Choudhary et al. |
| 7,718,832 B1 | 5/2010 | Schuetzle et al. |
| 7,772,450 B2 | 8/2010 | Iaccino et al. |
| 8,198,338 B2 | 6/2012 | Schulenberger et al. |
| 8,394,862 B1 | 3/2013 | Schuetzle et al. |
| 8,741,001 B1 | 6/2014 | Schuetzle et al. |
| 9,090,831 B2 | 7/2015 | Schuetzle et al. |
| 9,095,813 B2 | 8/2015 | Keith et al. |
| 9,476,002 B1 | 10/2016 | Schuetzle et al. |
| 9,611,145 B2 | 4/2017 | Schuetzle et al. |
| 9,631,147 B2 | 4/2017 | Schuetzle et al. |
| 10,478,806 B2 | 11/2019 | Schuetzle et al. |
| 2003/0113244 A1 | 6/2003 | Dupont et al. |
| 2005/0166447 A1 | 8/2005 | Corkwell et al. |
| 2006/0144755 A1 | 7/2006 | Benazzi et al. |
| 2008/0108716 A1 | 5/2008 | Ayasse |
| 2009/0300970 A1 | 12/2009 | Perego et al. |
| 2010/0160463 A1 | 6/2010 | Wang et al. |
| 2011/0044860 A1 | 2/2011 | Severinsky |
| 2012/0208902 A1 | 8/2012 | Kresnyak et al. |
| 2017/0321333 A1 | 11/2017 | Kuhl et al. |
| 2021/0230005 A1 | 7/2021 | Kim et al. |

OTHER PUBLICATIONS

Allam, R., et al., "Demonstration of the Allam cycle: an update on the development status of a high efficiency supercritical carbon . . . " Energy Procedia 114, 5949-5966 (2017).
Arakawa, H., "Catalysis research of relevance to carbon management: progress, challenges, and opportunities" Chem. Rev. 101, 953-996 (2001).
Artz, J., et al., "Sustainable conversion of carbon dioxide: An integrated review of catalysis and life cycle assessment" Chemical Reviews, 118, 434-504 (2018).
Ashcroft, A.T., et al., "Partial oxidation of methane to synthesis gas using carbon dioxide" Nature, 352, 255-256 (1991).
Bahmanpour, A.M., et al., "Cu—Al spinel as a highly active and catalyst for the reverse water gas shift reaction" ACS Catal., 9, 6243-6251 (2019).
Centi, G., et al., "Opportunities and prospects in the chemical recycling of carbon dioxide to fuels" Catalysis Today 148, 191-205 (2009).
Fan, M., et al., "Catalytic technology for carbon dioxide reforming of methane to syngas" ChemCatChem 1, 192-208 (2009).
Choudhary, V.R., et al., "Energy efficient methane-to-syngas conversion with low H2/CO ratio by simultaneous catalytic reactions . . . " Catalysis Letters, 32, 391-396 (1995).
Daza, Y.A. et al., "CO2 conversion by reverse water gas shift catalysis: Comparison of catalysts, mechanisms . . . " Royal Society of Chemistry Advances, 1-31 (2016).
Hill, M.R., "How to make renewable natural gas" 2018 AGA-EPA RNG Workshop (Oct. 23, 2018).
Intergovernmental Panel on Climate Change: IPCC special report on CO2 capture and storage, Cambridge University Press, Cambridge (2005).
Jafari, M., et al., "Plant-wide simulation of an integrated zero-emission process to convert flare gas to gasoline" Gas Processing Journal, 6, 1-20 (2018).
Jiang, Z., et al., "Turning carbon dioxide into fuel" Phil. Trans. R. Soc. A, 368, 3343-3364 (2010).
Kothandaraman, J., et al., "Conversion of CO2 from air into methanol using a polyamine and a homogeneous ruthenium catalyst" J. Am. Chem. Soc. 138, 778-781 (2016).
Li, W., et al., "A short review of recent advances in CO2 hydrogenation to hydrocarbons over heterogeneous catalysts" RSC Adv., 8, 7651 (2018).
Lortie, M., "Reverse water gas shift reaction over supported Cu—Ni nanoparticle catalysts" Dept. of Chem. and Bio. Eng. M.S. Thesis, University of Ottawa, Canada (2014).
Marti, C., et al., "Simulation of methane production from carbon dioxide . . . " ICCSA 2016: Computational Science and Its Applications—ICCSA, 319-333 (2016).
Melaina, M.W., et al., "Blending hydrogen into natural gas pipeline networks: a review of key issues" National Renewable Energy Laboratory, Technical Report #5600-51995 (2013).
Messias, S., et al., "Electro-chemical production of syngas from CO2 at pressures up to 30 bars in electrolytes containing ionic liquid" React. Chem. Eng., 4, 1982-1990 (2019).
Mikkelsen, M., et al., "The teraton challenge—a review of fixation and transformation of carbon dioxide" Energy Environ. Sci. 3, 43-81 (2010).
National Academy of Sciences, "Chemical Utilization of CO2 into Chemicals and Fuels, Gaseous Carbon Waste Streams Utilization" Nat'l Academies Press, Washington D.C. (2019).
Olah, G. A., et al., "Chemical recycling of carbon dioxide to methanol and dimethyl ether—from greenhouse gas to renewable, . . . " J. Org. Chem. 74, 487-498 (2009).
Owen, R. E., et al., "Kinetics of CO2 hydrogenation to hydrocarbons over Iron-Silica catalysts" Physical Chemistry, 18, 3211-3218 (2017).
Pan, X., et al., "Enhanced ethanol production inside carbon-nanotube reactors containing catalytic particles" Nat. Mater. 6, 507-511 (2007).
Ruckenstein, E., et al., "Combination of CO2 reforming and partial oxidation of methane over NiO/MgO Solid Solution" Industrial & Eng. Chem. Res., 37, 1744-1747 (1998).
Sakakura, T., et al., "Transformation of carbon dioxide" Chem. Rev. 107, 2365-2387 (2007).
Safriet, D., "Emission factor documentation for AP-12, Section 9.12.2 Wines and Brandy" U.S. EPA, Office of Air Quality, Research Triangle Park, NC (Oct. 1995).
Semelsberger, T.A., et al., "Dimethyl Ether (DME) as an alternative fuel" Journal of Power Sources 156, 497-511 (2006).
Socalgas, "Renewable natural gas (RNG) gas quality standards" (www.socalgas.com/rg) (2017).
Schuetzle, D., et al., "Solar reforming of carbon dioxide to produce diesel fuel" DOE report #DE-FE0002558 (2010).
Schuetzle, D., "Historical and predicted global climate changes . . . " 2018 Global Climate Action Summit, San Francisco, CA, www.researchgate.net (Apr. 24, 2017 & Jan. 26, 2020 update).
Vogt, C., et al., "The renaissance of the Sabatier reaction and its applications on Earth and in space" Nature Catalysis, 2, 188-197 (2019).
Wang, W., et al., "Recent advances in catalytic hydrogenation of carbon dioxide" Chem. Soc. Rev, 40, 3703-3727 (2011).
Wang, Y., et al., "High temperature solid oxide H2O/CO2 co-electrolysis for syngas production" Fuel Processing Technology, 161 (2016).

(56) References Cited

OTHER PUBLICATIONS

Williamson, D., et al., "N-doped Fe for combined RWGS-FT CO2 hydrogenation" 7, 7395-7402, ACS Sustainable Chem. Engineering (2019).
Wiecław-Solny, L., et al., "The technological research progress of amine-based CO2 capture" Polityka Energ. 16, 229-240 (2013).
Wikipedia: Energy density (2022) (www.en.wikipedia.org/wiki-/Energy_density).
Zaki, T., et al., "Natural gas origin, composition and processing: a review" Journal of Natural Gas Science and Engineering 34 (2016).
Zhang, J., et al., "Development of stable bimetallic catalysts for carbon dioxide reforming of methane" Journal of Catalysis, 249, 300-310 (2007).
Zhu, Q., "Developments on CO2-utilization technologies" Clean Energy, 3, 85-100 (2019).
Bavel, "Integrating CO2 Electrolysis into the Gas-to-Liquids-Power-to Liquids Process" 2597-2601. ACS Energy Letters. Web. Jul. 24, 2020.

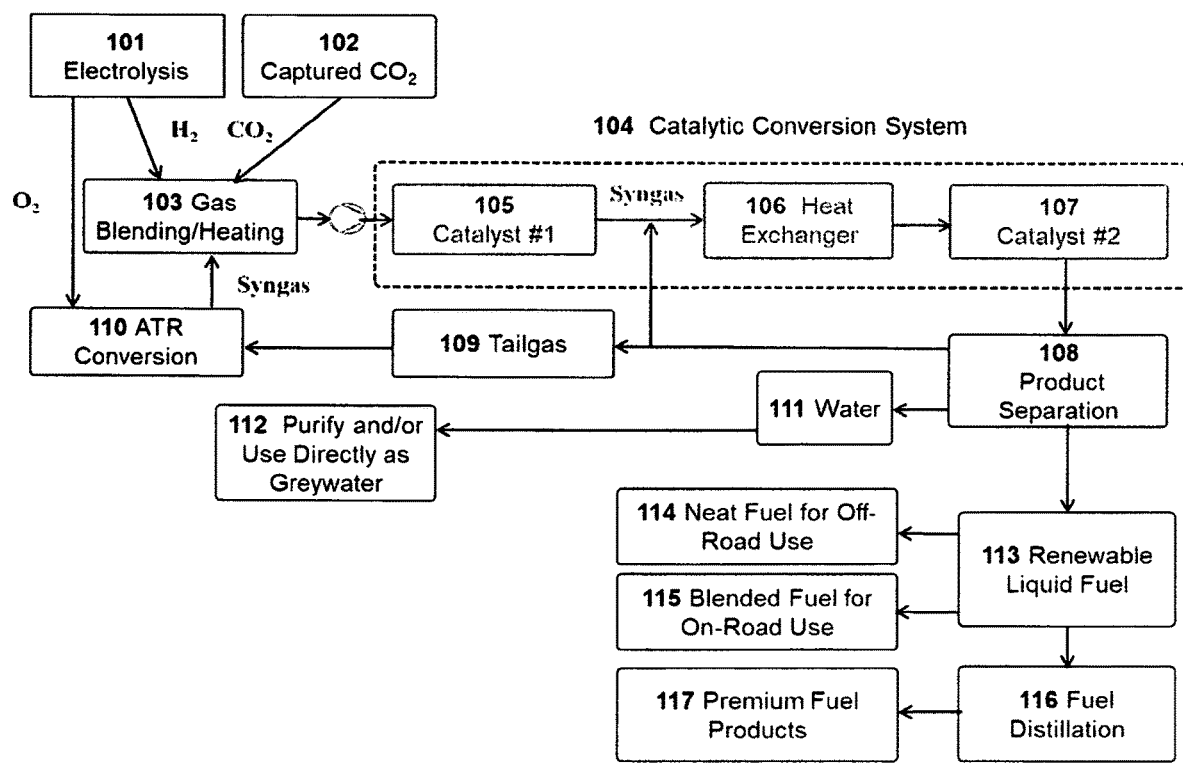
FIG. 1 – Process Flow Diagram for the Improved Catalysts and Processes used for the Direct Production of Liquid Fuels from $CO_2$ and Green $H_2$

FIG. 2 – Potential Reactions and Side Reactions for the Catalytic Conversion of $CO_2$ and $H_2$ to CO

| |
|---|
| 201. $CO_2$ Hydrogenation ($CO_2 + H_2 = CO + H_2O$) ($\Delta H_{298}$ = +42.1 kJ/mole) |
| 202. $CO_2$ Hydrogenation ($CO_2 + 4H_2 = CH_4 + 2H_2O$) ($\Delta H_{298}$ = -165.0 kJ/mole) |
| 203. $CH_4$ Dry Reforming ($CO_2 + CH_4 = 2CO + 2H_2$) ($\Delta H_{298}$ = +247.0 kJ/mole) |
| 204. $C_2H_6$ Dry Reforming ($2CO_2 + C_2H_6 = 4CO + 3H_2O$) ($\Delta H_{298}$ = +134.0 kJ/mole) |
| 205. CO Hydrogenation ($CO + 2H_2 = CH_4 + H_2O$) ($\Delta H_{298}$ = -206.1 kJ/mole) |
| 206. $CH_4$ Steam Reforming ($CH_4 + H_2O = CO + 3H_2$) ($\Delta H_{298}$ = +206.1 kJ/mole) |
| 207. $C_2H_6$ Steam Reforming ($C_2H_6 + 2H_2O = 2CO + 5H_2$) ($\Delta H_{298}$ = +136.0 kJ/mole) |
| 208. Water Gas Shift ($CO + H_2O = H_2 + CO_2$) ($\Delta H_{298}$ = -41.2 kJ/mole) |
| 209. $CO_2$ Reduction (coking) ($CO_2 + 2H_2 = C + 2H_2O$) ($\Delta H_{298}$ = -90.1 kJ/mole) |
| 210. $CH_4$ Reduction (coking) ($CH_4 + H_2 = C + 3H_2$) ($\Delta H_{298}$ = -165.0 kJ/mole) |
| 211. CO Reduction (coking) ($CO + H_2 = C + H_2O$) ($\Delta H_{298}$ = -131.3 kJ/mole) |
| 212. CO Reduction (coking) ($2CO = C + CO_2$) ($\Delta H_{298}$ = -172.4 kJ/mole) |
| 213. Methane Cracking ($CH_4 = 2H_2 + C$) ($\Delta H_{298}$ = +74.8 kJ/mole) |

EFFICIENT 2-STEP PROCESS FOR THE DIRECT PRODUCTION OF LIQUID FUELS FROM CARBON DIOXIDE AND HYDROGEN

FIELD OF THE INVENTION

This innovation describes an efficient 2-step process for the direct production of liquid fuels from captured $CO_2$ and green $H_2$. The green $H_2$ is produced by water electrolysis in which the power is derived from low-carbon sources. The first step in this 2-step process is the production of green syngas from captured $CO_2$ and the green $H_2$ using an improved catalyst. This improved catalyst is synthesized by the impregnation of one or more of the following elements (Ba, Ca, Co, Fe, Mg, Mn, Ni and Zn) on a metal-alumina spinet consisting of magnesium aluminate, calcium aluminate, strontium aluminate, potassium aluminate or sodium aluminate up to a concentration of about 35 parts-by-weight and calcining of the impregnated spinel up to 2,150° F. This improved catalyst converts $H_2$ and $CO_2$ mixtures to syngas with a $CO_2$ to CO conversion efficiency of 65% or greater and a CO selectivity of better than 98% at 150-350 psi and 1,650° F. The second catalyst directly produces liquid fuels from the syngas. The liquid fuels are comprised primarily of $C_5$-$C_{23}$ aliphatic hydrocarbons with a nominal concentration of wax ($C_{24}$+ hydrocarbons). Since this second catalyst operates efficiently at 250-350 psi, the first and second catalyst can be operated at the same pressure. The tailgas ($C_1$-$C_5$ HC's, $H_2$, CO and $CO_2$) from the catalytic process is partially oxidized with $O_2$ from the electrolysis (autothermal reforming [ATR]) to produce additional syngas, $CO_2$ and heat. This commercial-scale process is applicable to the conversion of $CO_2$ collected from traditional air blown power plants, gasification plants, oxy-combustion plants, cement plants, grain fermentation plants, natural gas wellheads, chemical refineries, petroleum refineries, secondary oil recovery processes and other plants that produce $CO_2$ emissions as well as $CO_2$ collected from ambient air. The liquid fuels produced include premium kerosene, diesel, jet, and gasoline and can be further processed to produce specialty chemicals including normal alkanes, normal 1-olefins, normal 1-hydroxy alkanes, solvents, lubricants and high-performance waxes. The reduction in greenhouse gas emissions for the production of these liquid fuels and chemicals varies from about 50-130%, depending upon the $CO_2$ source and the source of the power used for $H_2$ production. In addition to reducing greenhouse gas emissions, the synthetic fuels reduce criteria pollutant emissions. This simplified 2-step catalytic process is durable, efficient and maintains a relatively constant level of fuel productivity over long periods of time without requiring catalyst re-activation or replacement.

BACKGROUND OF THE INVENTION

This invention is primarily focused on improved catalysts and associated processes that efficiently and economically convert $CO_2$ and $H_2$ mixtures directly to liquid fuels that reduce greenhouse gas emissions. These liquid fuels are often referred to as low carbon liquid fuels (LCLF), net zero carbon fuels, zero carbon fuels, ultra-low carbon fuels, or green fuels.

There are several reasons why fossil fuels remain so popular (Fulkerson et al. 1990).

1. They are available in one form or another in virtually all regions globally since the infrastructure for gaseous and liquid fuels distribution is extensive.
2. They can be used effectively to provide energy for a myriad of applications at every scale.
3. They are without equal as fuels for transportation since they are portable and contain a considerable amount of stored chemical energy. Therefore, liquid fuels will continue to be the overwhelming energy source for transportation.

However, since the production and combustion of fossil fuels produce significant quantities of the greenhouse gases, $CO_2$ and $CH_4$, a global objective has been to replace fossil fuels with low carbon liquid fuels (LCLF) and/or low carbon natural gas (LCNG) (Schuetzle, 2018).

Although $CO_2$ can be converted to low carbon natural gas (LCNG) (Marti et al, 2016; Hill, 2018), there are several advantages to the conversion of $CO_2$ to LCLF instead of LCNG as follows:

1. The energy densities of diesel and gasoline fuels are about 38.6 and 34.2 MJ/liter, respectively. These energy densities are much higher than that of $CH_4$ (9.0 MJ/liter @ 250 bar); $H_2$ (5.3 MJ/liter @ 690 bar); dimethyl ether (21.2 MJ/liter @ 5 bar); methanol (15.6 MJ/liter); lithium-ion batteries (1.76 MJ/liter); and lead acid batteries (0.56 MJ/liter) (Wikipedia, 2019).
2. The production of $CH_4$ from $CO_2$ requires nearly twice as much $H_2$ as the production of liquid fuels from $CO_2$.
3. Diesel and gasoline fuels can be stored at or near atmospheric pressure compared to 200-400 bars for $CH_4$ and 340-690 bars for $H_2$.
4. The global distribution infrastructure of liquid fuels is extensive and they can be transported easily to nearly any location on the planet.
5. It is challenging to produce synthetic $CH_4$ that can meet natural gas pipeline standards (Zhou et al, 2010; Melaina et al, 2013; Zaki et al, 2016; SoCalGas, 2019).

As a result, there has been an increasing interest in the development of efficient and economical technologies for the conversion of $CO_2$ to liquid fuels (Arakawa et al, 2001; Olah et al, 2005; Sakakura et al, 2007; Centi et al, 2009; Olah et al, 2009; Mikkelsen et al, 2010; Artz et al, 2018; Li et al, 2018).

This improved catalyst and process offers the intriguing possibility of using primary energy from renewable, carbon-free sources (such as electricity derived from solar, wind, wave/tidal, hydro or nuclear) to convert $CO_2$, in association with hydrogen into high-density vehicle fuels that are compatible with our current transportation infrastructure. In addition, this next-generation technology will help the expansion of more efficient power plants that produce little or no emissions such as oxy-combustion plants. Oxy-combustion plants refer to power plants that produce power from natural gas and oxygen, whose effluent is a nearly pure $CO_2$ stream (instead of a diluted $CO_2$ stream as is produced from traditional power plants).

Its real attraction is that this approach offers the prospect of significantly reducing the carbon emissions from transportation systems without the paradigm shift in infrastructure required by electrification of the vehicle fleet or by conversion to a hydrogen economy (Pearson et al. 2009).

Most of the prior art on the development of $CO_2$ to liquid fuels has focused on the production of gasoline and diesel fuels as "drop-in" fuels. Dimethyl ether (DME) is a potential low-emission fuel for diesel engines but it is not a "drop-in" fuel since diesel engines must be modified for its use and the fueling infrastructure has not been developed (Semelsberger, 2006).

Although methanol has been proposed for many years as a potential liquid fuel for engines, it has not been accepted as a fuel since it is highly flammable, toxic and its combustion produces toxic and carcinogenic formaldehyde emissions. Instead, it is used primarily as an intermediate chemical product for the production of liquid fuels or chemicals.

The production of "drop-in" liquid fuels from mixtures of $H_2$ and $CO_2$ typically requires the following processes.
1. The conversion of the $H_2/CO_2$ mixture to syngas
2. The conversion of the syngas to fuels that meet ASTM and other fuel specifications (Worldwide Fuel Charter, 2019). This process usually requires two or more main conversion processes.

In order for $CO_2$ to liquid fuel processes to be commercially viable it is important that manufactured catalysts, for conversion of $H_2$ and $CO_2$ mixtures to syngas, meets one or more of the quality and performance specifications listed below in Table 1.

Table 1—Quality and Performance Specifications Established for the Catalytic Conversion of $H_2/CO_2$ Mixtures to Syngas The catalyst contains low-cost constituents (no [or nominal] rare metals).
It can be economically manufactured in multiple ton quantities.
The catalyst is robust (e.g., Rockwell hardness greater than Mohr 04-05).
It is chemically and physical stable up to about 2,150° F.
It can be loaded readily into catalytic reactors (e.g. tubular or packed bed reactors).
The pressure drop from the top to the bottom of the catalytic reactor is acceptable.
The catalyst activation (e.g., reduction with $H_2$) can be carried out in-situ.
The $CO_2$ to CO conversion efficiency is greater than about 60% per pass, but preferably greater than about 70% per pass at space velocity's of greater than about 2,500 $hr^{-1}$.
The CO production selectivity is greater than about 80%, but preferably greater than about 90%.
It does not coke (e.g. form carbon deposits).
It has a long lifetime and doesn't require systematic re-activation (reduction).

Two approaches have been described in the prior art for the conversion of $CO_2$ to syngas. The first and most widely described approach employs catalytic processes for the conversion of mixtures of $CO_2$ and $H_2$ to syngas. This method is typically referred to as "$CO_2$ hydrogenation" or "reverse water gas shift (RWGS)" (Senderens et al, 1902; Daza et al, 2016; Vogt et al, 2019). The second approach involves electrolysis processes for the conversion of mixtures of $CO_2$ and $H_2O$ to syngas (Wang et al, 2016).

Catalytic Conversion of $H_2/CO_2$ Mixtures to Syngas—Many patent applications, patents and publications describe the development of catalysts for the conversion of $H_2$ and $CO_2$ mixtures to syngas. This prior art is evaluated with respect to the quality and performance specifications outlined in Table 1.

Iwanani et al (1993) developed a catalyst comprised of transition metals with rare metals (such as Ni, Fe, Ru, Rh, Pt, W, Pd, Mo) on zinc oxide for the reduction of $CO_2$ and $H_2$ mixtures to CO. They achieved relatively low conversions of up to 37% without significant loss of catalyst activity after 150 hrs but testing for longer periods was not carried out.

Chen et al (2015) reported the synthesis of a nano intermetallic catalyst ($InNi_3CO_{0.5}$) that proved to be active and selective for the RWGS reaction. The catalyst was fabricated by carburizing the In—Ni intermetallic base which produced dual active sites on the catalyst surface. They achieved a moderate 52-53% $CO_2$ conversion for 150 hrs at 600° C. and gas hourly velocities of 300,000 ml/g (cat)/hr. Testing of this catalyst for longer periods was not carried out.

Bahmanpour et al (2019) tested a Cu impregnated Cu—Al spinel as a potential catalyst for the hydrogenation of $CO_2$ with $H_2$ into syngas. They used co-precipitation followed by hydrogen treatment to form the Cu—Al spinel in different Cu/Al weight ratios. A Cu to Al ratio of 4 to 1 was found to be the most efficient for $CO_2$ conversion. However, they observed a relatively low $CO_2$ conversion rate of about 45% at 600° C. after a 40 hour test. Since copper containing catalysts tend to deactivate by sintering at high temperatures such catalyst formulations need to be tested for 1,000 hrs or more to assess potential commercial viability. This is the only work published to date on the synthesis and performance of metals impregnated and calcined on metal-alumina spinels.

Electrochemical Conversion of $CO_2/H_2O$ Mixtures to Syngas—The electrochemical conversion of $CO_2$ has been a dynamic field of research (Zhu, 2019). Much of the R&D effort has centered on the modification of fuel cells (Sunfire, 2016) and PEM and alkaline electrolysis systems (Messias et al, 2019).

PEM & Alkaline Electrolysis—Opus 12 has developed a PEM electrolyzer that converts mixtures of $CO_2$ and $H_2O$ to a mixture of sixteen $C_1$-$C_3$ oxygenated hydrocarbons (alcohols, ketones, aldehydes and acids) (Kuhl et al, U.S. Patent Application Publication 2017/0321333). The separation of this complex mixture into specific chemical compounds requires costly refining processes. If that separation is successful, ethanol is the only suitable product that can be used as a fuel (e.g. blended with gasoline).

Fuel Cells—Sunfire has developed a process based on high-temperature co-electrolysis of $CO_2$ and $H_2O$ using solid oxide electrolysis cells (SOEC) to produce syngas. The SOEC operates at high pressure (>1 MPa) and high temperature (>800° C.). The syngas is then converted to long-chain hydrocarbons using traditional Fischer-Tropsch processes. The waxes are converted into gasoline and diesel fuels using a two-step catalytic refining process. Therefore, three-steps are required for Sunfire's production of "drop-in" fuels and this process requires complex wax upgrading or refining.

In the current art, four principal processes for the conversion of $CO_2$ to "drop-in" liquid fuels are possible:

One-Step Processes
1. $CO_2$ is converted directly to liquid fuels using catalytic or electrochemical processes.

Two-Step Processes
1. $CO_2$ is converted to syngas using catalytic or electrochemical processes.
2. The syngas is converted directly to liquid fuels using a second catalyst.

Two-Step Processes
1. $CO_2$ is converted to primary chemical intermediates using catalytic or electrochemical processes;
2. The chemical intermediates are converted directly to liquid fuels using a second catalyst.

Three-Step Processes
1. $CO_2$ is converted to syngas using catalytic or electrochemical processes;
2. The syngas is converted to a primary chemical intermediate (e.g. wax; methanol, etc.);
3. The purified intermediate is converted directly to liquid fuels.

Four-Step Processes
1. $CO_2$ is converted to syngas using catalytic or electrochemical processes;
2. The syngas is converted to a primary chemical intermediate (e.g. wax; methanol, etc.);
3. The purified intermediate is converted to liquid fuels using two major chemical processes Four-Step Processes
1. $CO_2$ is converted to syngas using catalytic or electrochemical processes.
2. The syngas is converted to a mixture of organic intermediates (e.g. wax; methanol, etc.);
3. Separation processes are employed to generate the desired purified intermediate;
4. The purified intermediate is converted to liquid fuels.

The prior art for the one-, two-, three-, and four-step processes are summarized and assessed with respect to the quality and performance specifications outlined in Table #1.

One-Step Processes—Most of the effort to convert $CO_2$ to liquid hydrocarbon fuels in a single reactor has been to develop a catalyst that first generates CO from $CO_2$ by hydrogenation. The CO then reacts with $H_2$ on the same catalyst to form liquid fuels through a mechanism based on a conventional Fischer-Tropsch (F-T) catalytic reaction. One of the challenges associated with this F-T process using $CO_2$ is that there is only a small concentration of CO present during the reaction. This limits chain growth and consequently the product distribution is normally rich in light hydrocarbons, which are not suitable as liquid fuels. To date, most research has focused on the use of iron-based catalysts, which are active for the reverse water gas-shift reaction and F-T chemistry (National Academy of Sciences, 2019).

Landau et al (Australian patent application 2015/203898) described a 20% $Fe_2O_3$ on iron-spinel catalyst. The catalyst particle size varied from 100 um to 3.0 mm. This catalyst was tested using syngas with an $H_2/CO_2$ ratio of 2.0-3.0/1.0, a very low space velocity of about 2.0 $hr^{-1}$, a temperature of 325-350° C., and a pressure of 20-40 atmospheres. The maximum conversion of $CO_2$ was 36%. The selectivity of the products was: CO (13%), $CH_4$ (9%), $C_2$-$C_5$ (44%) and $C_6$-$C_{27}$ HC's (25%). The olefin/paraffin ratio of the $C_6+$ hydrocarbons was about 5/1. This catalyst does not produce a "drop-in" fuel that meets ASTM specifications, and it does not meet the catalyst quality and performance specifications listed above.

Wang et al. (2013) described a $Fe/ZrO_2$ catalyst for catalyzing the hydrogenation of $CO_2$ that produced primarily $CH_4$ and $C_2$-$C_4$ paraffins. The selectivity for production of liquid-phase hydrocarbons was very low.

Wei et al. (2018) described an iron-based catalyst for the one-step conversion of $CO_2$ into iso-paraffins. The conversion efficiency of $CO_2$ was only 26% with a CO selectivity of about 17%. Coke (carbon) deposition inside the micropores of the catalyst caused a rapid decline of iso-paraffin yield with time.

Williamson et al. (2019) described the performance of a one-step catalyst comprised of iron nano-particles deposited on carbon nanotubes. The catalysts were calcinated at 400° C. for 1 hour or 570° C. for 40 minutes in air and activated with $H_2$ at 400° C. for 3 hours. The catalysts were tested in laboratory reactors at 370° C. and 221 psi using a $H_2/CO_2$ mixture of 3.0/1.0. The average $CO_2$ conversion was 54% with CO and hydrocarbon selectivity's of 30% and 70%, respectively. The average composition of the hydrocarbon products was 43% $CH_4$, 55% $C_2$-$C_4$ and 2.0% $C_5+$ hydrocarbons.

Pan et al. (2007) described the use of an Rh catalyst supported on carbon nanotubes in a tubular reaction for the production of ethanol from mixtures of $CO_2$ and $H_2$ at a very low space velocity of about 13 $hr^{-1}$. In addition to ethanol, this catalyst produced a complex mixture of oxygenated hydrocarbons including methanol, acetaldehyde, acetone, isopropanol and acetic acid. The problem with this catalyst is that it is not amenable to scale up to commercial scale due to a high catalytic reactor pressure drop, the low space velocity, and the production of a complex mixture of oxygenated hydrocarbons.

Two-Step Processes—Shulenberger et al (U.S. Pat. No. 8,198,338) described a process for the conversion of $CO_2$ into gasoline. $H_2$ and $CO_2$ (2.0/1.0 molar ratio) were converted to methanol using a $Cu/ZnO/Al_2O_3$ catalyst in a catalytic reactor operated at about 50 bar pressure and 500° C. Since the operating pressure was low, the selectivity for methanol production was only about 10%. The methanol produced from the first catalytic process was fed into another catalytic reactor containing a ZSM-5 catalyst and operated at about 4 bar pressure and 390° C. for the conversion of methanol to gasoline. The conversion efficiency of the two-step process and the chemical and physical composition of the gasoline were not described. However, as based upon the selectivity of methanol production in the first reactor, the selectivity for gasoline production was estimated to be less than 10%.

Three-Step Processes—Sunfire carried out a pilot system to use electrolytic conversion of $CO_2$ and $H_2O$ using solid oxide electrolysis cells (SOEC) to produce syngas (Zhu, 2019). The syngas was then converted to long-chain hydrocarbons using traditional Fischer-Tropsch processes. The waxes were converted into gasoline and diesel fuels using a two-step catalytic refining process. Therefore, three-steps were required for Sunfire's pilot plant related to "drop-in" fuels.

Four-Step Processes—Several four-step processes have been described in the current art. One approach is to produce a chemical intermediate such as methanol from $H_2/CO_2$ mixtures using a one-step process, followed by the conversion of the methanol to gasoline using a three-step process. Another approach is to produce syngas from $H_2/CO_2$ mixtures, followed by the Fischer-Tropsch conversion of the syngas to wax and then a two-step conversion of the wax to liquid fuels.

Kothandaraman et al (2016) used a polyamine (PEMA) in tetrahydrofuran (THF) to capture $CO_2$. Although this amine has good $CO_2$ capture efficiency, amines are known to deactivate catalysts. The captured $CO_2$ was converted to methanol in the solution using a Ruthenium PNP pincer catalyst. This catalyst is a complex of Ruthenium with an organic ligand that surrounds the Ruthenium. This process was tested in the laboratory using a $H_2/CO_2$ reactant ratio of 3.0/1.0, a pressure of 75 atmospheres and a temperature of 145° C. The carbon conversion of $CO_2$ to $CH_3OH$ was 65%.

A plant to demonstrate this process was commissioned in Svartsengi, Iceland during 2012. The $H_2$ is produced electrochemically from $H_2O$ using 5.0 megawatts of geothermal power. The $CO_2$ is captured from the Svartsengi power plant in Iceland. The methanol output is about 50,000 liters/year.

Gasoline can be produced from this methanol using the three-step Exxon-Mobil patented process (Jafari, 2018). This process employs three catalytic reactors: Catalytic conversion #1: methanol to dimethyl ether; Catalytic conversion #2: dimethyl ether to $C_2$-$C_5$ olefins; Catalytic conversion #3: $C_2$-$C_5$ olefins to gasoline. The MTG gasoline is typically comprised of 53% paraffins, 12% olefins, 9% napthenes, 26% aromatics, 0.3% benzene and no sulfur. The octane ratings (RON+MON)/2 are 87 and the RVP (psi) is 9.0.

In conclusion, no prior art has been identified for which "drop-in" liquid fuels can be produced in two primary steps from $CO_2/H_2$ mixtures which meet the performance and quality specifications summarized in Table 1.

Metal-Alumina Spinets—Bahmanpour et al (2019) has published the only prior art to date on the performance of a metal impregnated and calcined on a metal-alumina spinel substrate. They synthesized a CuO on $CuAl_2O_4$ spinel in which the Cu/Al ratio was 4/1. A relatively low $CO_2$ conversion rate of 47% was observed at 600° C. with no detectable deactivation after a 40 hr. test. However, copper containing catalysts tend to deactivate by sintering at high temperatures. In addition, candidate catalyst formulations need to be tested for 1,000 hrs or more to assess potential commercial viability.

No other prior art has been published on the RWGS activity of other metals impregnated and calcined on metal spinels.

Tail-Gas Conversion—The one-step, two-step, three-step and four-step processes produce tailgas that typically consists of $C_1$-$C_5$ hydrocarbons and $CO_2$ as well as unconverted $H_2$ and CO. This tailgas needs to be either used as energy for a commercial-scale plant or converted to additional syngas.

The predominant process for conversion of tail-gas to syngas is by means of Steam Methane Reforming (SMR) process. However, steam reforming has several disadvantages. It is a highly endothermic reaction and excess steam is required to prevent or delay deactivation from carbon deposition. Consequently, the high energy requirement for SMR results in a high cost of production of this additional synthesis gas. In addition, SMR processes produce $CO_2$ from combustion of fuel gas to fire the burners in the SMR.

Catalytic partial oxidation (PDX) of tail-gas to syngas has several advantages over SMR. Since the oxidation of hydrocarbons to synthesis gas mixtures is exothermic, this process is much more energy efficient than both the steam and dry reforming processes (Gaffney et al, U.S. Pat. No. 6,402, 989). However, PDX has several potential disadvantages as follows:

1. Relatively pure oxygen is needed, the source of which is usually from its cryogenic separation from air.
2. The PDX process can be highly exothermic which can lead to catalyst hot spots which can damage the catalyst or causing thermal runaways.

Autothermal reforming (ATR) of tail-gas to syngas is another process that can be used for conversion of the tail-gas. The partial oxidation occurs in the inlet of the reactor, which provides heat for steam reforming reaction. As a result, there is no need to supply heat to the reactor (Ashcroft (1991); Choudhary (1995); and Ruckenstein (1998)).

Cobalt-nickel catalysts on alumina have been found to show superior performance for ATR of methane in terms of activity, stability and synergy when compared to other catalysts. However, some carbon formation is observed when mixtures of $CH_4$, $CO_2$ and $O_2$ are reformed at about 1,300° F. and 15 psi (Foo (2012) and Zhang (2007)).

SUMMARY OF THE INVENTION

In one aspect, the present invention provides a process for the conversion of carbon dioxide into a liquid fuel, wherein the process comprises the steps of: a) introducing a gaseous mixture of carbon dioxide and hydrogen, or a mixture of carbon dioxide, hydrogen and light hydrocarbons, into a first catalytic reactor in a catalytic conversion system to produce syngas, wherein the first catalyst consists of the impregnation of one or more of the following elements (Ba, Ca, Co, Fe, Mg, Mn, Ni and Zn) on a metal-alumina spinel consisting of magnesium aluminate, calcium aluminate, strontium aluminate, potassium aluminate or sodium aluminate up to a concentration of about 35 parts-by-weight (e.g., 1 part-by-weight to 35 parts-by weight, 5 parts-by-weight to 35 parts-by-weight or 10 parts-by weight to 35 parts-by weight) and calcining of the impregnated spinel up to 2,150° F. (e.g., 1,000° F. to 2,150° F., 1,500° F. to 2,150° F., or 1,750° F. to 2,150° F.); and b) introducing the syngas into a second catalytic reactor in the catalytic conversion system to produce tailgas, water and liquid fuel, wherein the second catalyst comprises about 2 to about 25 parts-by-weight (e.g., 3 to 25 parts-by-weight, 5 to 25 parts-by-weight or 10 to 25 parts-by-weight) of an element wherein the element is selected from a group of elements consisting of cobalt, iron, magnesium, manganese, calcium, barium, copper and zinc, and from about 0.1 to about 5 parts-by-weight (e.g. 0.2 to 5 parts-by-weight, 1 to 5 parts-by-weight or 2 to 5 parts-by-weight) of at least one metal selected from a group consisting of cerium, ruthenium, lanthanum, platinum, or rhenium per 100 parts-by-weight of a support selected from a group consisting of silica, alumina, and combinations thereof thereby producing liquid fuel, tailgas and water; c) separating the liquid fuel, tailgas and water from one another, thereby producing the liquid fuel.

In another aspect, the present invention provides a catalyst for the conversion of carbon dioxide into syngas wherein the $H_2/CO_2$ introduced into the first catalytic reactor has a volume ratio of about 2.0-4.0 (e.g., 2.0-4.0), and in which the catalytic reactor is operated at temperatures in the range of about 1,550 to 1,900° F. (e.g., 1,550 to 1,900° F.); at pressures in the range of about 100-400 psi (e.g., 100-400 psi); and space velocities above about 1,000 $hr^{-1}$ (e.g., 1,000 $hr^{-1}$ to 50,000 $hr^{-1}$, 2,500 $hr^{-1}$ to 25,000 $hr^{-1}$ or 5,000 $hr^{-1}$ to 15,000 $hr^{-1}$).

In another aspect, the present invention provides for the direct production of a liquid fuel, wherein the process comprises the steps of: a). producing $H_2$ and $O_2$ from the electrolysis of water wherein the power for the electrolysis is generated from a renewable or low-carbon source, and wherein the renewable or low carbon source is selected from a group of sources consisting of wind, solar, geothermal, hydro, ocean currents, biomass, flare gas, nuclear, off-peak power from a fossil fuel plant, and power produced by an oxy-combustion plant.

In another aspect, the present invention provides a process for the production of a liquid fuel, wherein the process comprises the steps of: a) producing $H_2$ and $O_2$ from the electrolysis of water; combusting waste polymeric materials (e.g. plastics) and/or other waste materials (e.g. biomass, paper, etc.) with some of the oxygen produced from the electrolysis process; b) producing combustion gases comprising primarily carbon dioxide and water, along with heat; c) passing the hot combustion gases through a gas turbine generator, thereby generating electricity for operation of the 2-step catalytic process described herein; d) removing water and trace contaminants (e.g. S and Cl compounds) from the combustion gases to provide a purified $CO_2$ stream; e) blending this $CO_2$ with $H_2$ to provide an $H_2/CO_2$ mixture with a volume ratio of about 1.5/1.0 to 4.0/1.0; f) introducing this $H_2/CO_2$ mixture into the first catalytic reactor to produce syngas, g) introducing this syngas into the second catalytic reactor to produce tailgas, water and liquid fuel; h) separating the liquid fuel, tailgas and water from one another thereby producing the liquid fuel.

BRIEF DESCRIPTION OF THE DRAWINGS

FIG. 1 illustrates the process flow diagram for the improved catalysts and processes described herein for the direct production of liquid fuels from $CO_2$ and renewable $H_2$. It further illustrates an integrated conversion system and process for the production of low-carbon liquid fuels.

FIG. 2 summarizes the potential reactions that can occur when mixtures of $CO_2$ and $H_2$ are catalytically converted to CO.

DETAILED DESCRIPTION OF THE INVENTION

This invention relates to improved catalysts and processes for the efficient and economical conversion of $CO_2$ and $H_2$ mixtures directly to synthetic liquid fuels in two steps.

It has been discovered and reported herein that this improved catalyst consists of the impregnation of one or more of the following elements (Ba, Ca, Co, Fe, Mg, Mn, Ni and Zn) on a metal-alumina spinel consisting of magnesium aluminate, calcium aluminate, strontium aluminate, potassium aluminate or sodium aluminate up to a concentration of about 35 parts-by-weight and calcining of the impregnated spinel up to 2,150° F. These improved catalysts exhibit excellent $CO_2$ conversion efficiency's and CO selectivity's for the conversion of $H_2/CO_2$ mixtures to syngas.

FIG. 1 illustrates the process flow diagram for the improved catalysts and processes described herein for the direct production of liquid fuels from $CO_2$ and renewable $H_2$. It further illustrates an integrated catalytic converter and process for the production of low-C liquid fuels.

Electrolysis is used to generate $H_2$ 101. The power for $H_2$ production may be generated from, but not limited to, renewable and or low-carbon sources such as wind, solar, geothermal, hydro, ocean currents, biomass, flare-gas, nuclear and others. Other possible sources include efficient power produced from oxy-combustion plants.

Captured $CO_2$ 102 may be obtained from, but not limited to $CO_2$ collected from traditional air blown power plants, gasification plants, oxy-combustion power plants, cement plants, grain fermentation plants, natural gas well-heads, chemical refineries, petroleum refineries, secondary oil recovery processes and other plants that produce $CO_2$ emissions as well as $CO_2$ collected from ambient air.

$H_2$ from process 101; $CO_2$ from process 102; and syngas and heat (Q) from process 110 are mixed 103 in the proper proportions, heated, and input into the catalytic conversion system 104. Two innovative catalysts, catalyst #1 105 & catalyst #2 107 are incorporated in the catalytic conversion system 104.

Catalyst #1 105 is a high-surface area (>15 m²/g) catalyst which is synthesized by impregnation of one or more of the following elements (Ba, Ca, Co, Fe, Mg, Mn, Ni and Zn) on a metal-alumina spinel consisting of magnesium aluminate, calcium aluminate, strontium aluminate, potassium aluminate or sodium aluminate up to a concentration of about 35 parts-by-weight (e.g., 1 part-by-weight to 35 parts-by-weight, 5 parts-by-weight to 35 parts-by-weight or 10 parts-by weight to 35 parts-by weight) and calcining of the impregnated spinel up to 2,150° F. (e.g., 1,000° F. to 2,150° F., 1,500° F. to 2,150° F., or 1,750° F. to 2,150° F.). The improvements described herein include a manufacturing process that produces robust catalysts consisting of certain metal spinels that have been impregnated with one or more of the elements (Ba, Ca, Co, Fe, Mg, Mn, Ni and Zn).

Catalyst #2 107 is a catalyst that was developed for the direct production of liquid fuels from syngas as described by Schuetzle et al. in U.S. Pat. Nos. 8,394,862; 9,090,831; and 9,631,147. Catalyst #1 105 and catalyst #2 107 have been developed to operate at pressures in the range of about 100 to 350 psi (e.g., 100 psi to 350 psi).

Since catalyst #1 operates at a higher temperature than catalyst #1, a heat exchanger 106 is incorporated in the catalytic conversion system 104 to reduce the temperature of the gases to the operating temperature of catalyst #2 107. The products from the catalytic conversion processes 104 are separated by a product separator 108 into tailgas 109, water 111, and renewable liquid fuels 113.

Some of the tailgas 109 is recycled back to the catalytic conversion process 104 until the CO in the syngas reaches the desired conversion efficiency. The remaining tailgas 109 is combusted 110 with oxygen (Autothermal Reforming (ATR)) produced from the electrolysis system 101. The products from the ATR process 110 are syngas and heat. The syngas is blended with the other gases in 103 and the heat from 110 is used to help heat the gas blending/heating system 103. Additional heat is added to the gas blending system 103 to bring the gases to a temperature up to the operating temperature of catalyst #1 105.

The water (commonly referred to as catalyst reaction water) 111 can be used for greywater applications 112, or purified for the electrolysis process 101 and/or other uses. The renewable liquid fuel 113 can be used directly (neat) for off-road diesel engines 114, blended with petroleum derived diesel fuel 115, or distilled 116 into premium fuel products (e.g., #1 diesel, #2 diesel, #3 diesel and jet fuels) 117.

FIG. 2 summarizes the potential reactions that can occur when mixtures of $CO_2$ and $H_2$ are catalytically converted to CO. The catalyst described in this improved art has been developed to primarily produce CO by way of reactions 201 from mixtures of $CO_2$ and $H_2$ and $CO_2$ and $C_1$-$C_8$ hydrocarbons via reactions 203 and 204 (if present with the $CO_2$).

The improved catalyst and processes primarily produce CO from $CO_2$ and $H_2$ (reaction 201) or CO from $CO_2$ and hydrocarbons (reactions 203 and 204). These reactions are endothermic which means that heat needs to be added for the conversion to occur. As illustrated in FIG. 1, the first catalyst in the catalytic reactor is used to efficiently convert mixtures of $CO_2$ and $H_2$ to CO. This improved $CO_2$ reforming catalyst 105 predominantly produces CO with greater than about 95% selectivity at 150-300 psi. Since the first catalyst operates at a higher temperature than the second catalyst, a heat exchanger (FIGS. 1-106) is incorporated between the catalysts to reduce the temperature of the second catalyst to its ideal operating level.

A foremost advantage of this process is that catalysts #1 and #2 can be operated efficiently in series at similar pressures (recognizing that there is pressure drop between catalytic system #1 and catalytic system #2) which eliminates the need for compression between the two catalytic reactor systems.

Table 2 summarizes the selectivity's for CO and $CH_4$ production from an $H_2/CO_2$ mixture (3.4/1.0) at 1,650° F. and 300 psi for the $CO_2$ reforming catalyst. The $CO_2$ conversion efficiency is about 71% with a CO selectivity of about 100% and a methane selectivity of zero.

TABLE 2

The Selectivity's for CO and $CH_4$ Production with $H_2/CO_2$
(3.4/1.0) at 1,650° F. and 300 psi for the Improved $CO_2$
Reforming Catalyst after about 800 hours of operation.
$CO_2$ Reforming Catalyst Performance

| Component | Conversion/ Production (%) | Selectivity (%) |
|---|---|---|
| $CO_2$ | −71.0 | — |
| CO | +71.0 | 100 |
| $CH_4$ | 0 | 0 |

Table 3 summarizes the effect of pressure on the conversion of a mixture of $H_2$ and $CO_2$ (3.4/1.0) to CO at 1,650° F. As the pressure is increased from 150 to 300 psi, the CO selectivity is nearly 100% and the $CH_4$ selectivity is zero. However, the $CO_2$ conversion efficiency is reduced from about 78% at 150 psi to 73% at 300 psi.

TABLE 3

The Effect of Pressure on the Conversion Efficiency
of a $H_2/CO_2$ mixture (3.4/1.0) to CO at 1,650° F.
for the Improved $CO_2$ Reforming Catalyst

| Pressure (psi) | $CO_2$ Conversion (%) | CO Selectivity (%) | $CH_4$ Selectivity (%) | Other Products (%) |
|---|---|---|---|---|
| 150 | −78.0 | 100 | 0 | 0 |
| 300 | −71.0 | 100 | 0 | 0 |

The second catalyst 107 in the back end of the converter (FIG. 1) utilizes a catalyst that directly produces fuels from syngas.

This composition of the improved catalyst 107 contains from about 2 to about 25 parts-by-weight cobalt (e.g., 3 to 25 parts-by-weight cobalt, 5 to 25 parts-by-weight cobalt or 10 to 25 parts-by-weight cobalt) and from about 0.1 to about 5 parts-by-weight (e.g., 0.2 to 5 parts-by-weight, 1 to 5-parts-by-weight or 2.5 to 5 parts-by-weight) of at least one metal selected from a group consisting of cerium, ruthenium, lanthanum, platinum, or rhenium per 100 parts-by-weight of a support selected from a group consisting of silica, alumina, and combinations thereof.

Table 4 provides the relationship between the temperatures of catalyst #2 on the conversion of $CO_2$ in syngas produced from catalyst #1. Therefore, catalyst #2 converts some of the $CO_2$ not converted by catalyst #1, depending on the operating temperature.

TABLE 4

The Effect of Temperature on the Conversion
of $CO_2$ in Syngas by Catalyst #2

| T (° F.) | $CO_2$ Conversion (%) |
|---|---|
| 400 | 1.71 |
| 410 | 3.23 |
| 420 | 5.39 |
| 430 | 9.25 |
| 440 | 14.6 |
| 450 | 24.5 |

The $CO_2$ used as inputs to the process can be obtained from many different sources including $CO_2$ collected from traditional air blown power plants, gasification plants, oxy-combustion power plants, cement plants, grain fermentation plants, natural gas well-heads, chemical refineries, petroleum refineries, secondary oil recovery processes and other plants that produce $CO_2$ emissions. In addition, $CO_2$ can be collected from ambient air using direct air capture systems and desorbed into a relatively pure $CO_2$ stream for use in the improved 2-step process described herein.

$CO_2$ containing $C_2$-$C_6$ hydrocarbons can also be used as process inputs since these hydrocarbons will also be converted to liquid fuels. Such streams include natural gas condensates, gases from refinery processes and other gas streams that contain $CO_2$ and $C_2$-$C_6$ hydrocarbons.

The integrated process above requires a carbon dioxide input. In one embodiment, the carbon dioxide is supplied from the separation of the carbon dioxide in a flue gas stream using an alkylamine. Alkylamines used in the process can include mono-ethanolamine, diethanolamine, methyl-di-ethanolamine, disopropyl-amine, amino-ethoxy-ethanol, or combinations thereof. In another embodiment, the carbon dioxide is already present in natural gas feedstocks.

The manufacturing process for the first catalyst is important in that it produces a robust catalyst comprised of various impregnated spinels. This unique chemical structure leads to enhanced resistance to coking, when compared to conventional metal supported reforming catalysts. This also leads to enhanced resistance to syngas poisons such as sulfur and ammonia. In addition, this catalyst has enhanced catalytic activity at lower surface area compared to monometallic segregated catalyst phase, for example Ni on alumina. This catalyst requires no alkali promotion needed to curb the carbon deposition typically seen with feed gases as described herein. The catalyst is also operable in a variety of dry, steam, combined dry/steam and tri-reforming feeds. Mixes of higher hydrocarbon feedstocks are also achievable with this catalyst.

Manufacture of Catalyst #1—The improved catalyst is produced in two steps: 1). The high surface area (>15 m$^2$/g) metal-spinels (e.g., 15 m$^2$/g to 150 m$^2$/g, 20 m$^2$/g to 150 m$^2$/g or 25 m$^2$/g to 150 m$^2$/g) are synthesized by the impregnation of high surface area alumina with one of the following elements (Mg, Ca, Sr, K or Na) and calcining of the impregnated alumina up to 2,150° F. (e.g., 1,000° F. to 2,150° F., 1,500° F. to 2,150° F., or 1,650° F. to 2,150° F.), resulting in the formation of magnesium aluminate, calcium aluminate, strontium aluminate, potassium aluminate, or sodium aluminate; 2). One of these spinels is then impregnated with up to 35 wt. % (e.g., 1 part-by-weight to 35 parts-by weight, 5 parts-by-weight to 35 parts-by-weight or 10 parts-by weight to 35 parts-by weight) of one or more of the following elements (Ba, Ca, Co, Fe, Mg, Mn, Ni and Zn) followed by calcining up to 2,150° F. (e.g., 1,000° F. to 2,150° F., 1,500° F. to 2,150° F., or 1,750° F. to 2,150° F.). Three specific examples are provided below.

Example #1—The synthesis of the magnesium aluminate ($MgAl_2O_4$) is provided as the first example. High-surface area gamma-alumina ($Al_2O_3$) pellets are selected as the substrate for the synthesis of the spinel that are about 1-10 mm in diameter with a surface area greater than about 35 m$^2$/g. Enough magnesium acetate (Mg ($C_2H_3O_2$)$_2$ is dissolved in distilled water to produce a 1.0 mg/ml solution. About 100 ml of this solution is mixed with 100 g of the pellets and placed in a drying oven at 220° F. for 30 minutes. The impregnated pellets are calcined by heating in air at a rate of 15° F./min until a final temperature of 2,050° F. is reached in about 2 hrs. The mixture is kept at 2,050° F. for 30 minutes and cooled down to room temperature at a rate of about 15° F./min. The resulting product is an Mg-Alumina spinel ($MgAl_2O_4$). The other spinels may be synthesized in a similar manner using acetate or nitrate salts of calcium, strontium, potassium or sodium.

Example #2—The synthesis of 10 wgt % Mg on magnesium aluminate ($MgAl_2O_4$) in one step is provided as the first example. High-surface area gamma-alumina ($Al_2O_3$) pellets are selected as the substrate for the synthesis of the spinel that are about 1-10 mm in diameter with a surface area greater than about 35 m$^2$/g. Enough magnesium acetate (Mg ($C_2H_3O_2$)$_2$ is dissolved in distilled water to produce a 1.0 g/ml solution. About 180 ml of this solution is mixed with 100 g of the pellets and placed in a drying oven at 220° F. for 30 minutes. The impregnated pellets are calcined by heating in air at a rate of 15° F./min until a final temperature of 2,050° F. is reached in about 2 hrs. The mixture is kept at 2,050° F. for 30 minutes and cooled down to room temperature at a rate of about 15° F./min. The resulting product is a 10 wgt. % Mg impregnated Mg-Alumina spinel ($MgAl_2O_4$).

Example #3—The synthesis of 10 wgt % Mg and 2.5 wgt % Ca on magnesium aluminate ($MgAl_2O_4$) is provided as the next example. The magnesium aluminate synthesized in Example #1 is impregnated with a solution of magnesium acetate (Mg ($C_2H_3O_2$)$_2$) and calcium acetate (Ca ($C_2H_3O_2$)$_2$) resulting in 10 wgt % Mg and 2.5 wgt % Ca impregnated on the magnesium aluminate. The impregnated pellets are calcined by heating in air at a rate of 15° F./min until a final temperature of 2,050° F. is reached in about 2 hrs. The mixture is kept at 2,050° F. for 30 minutes and cooled down to room temperature at a rate of about 15° F./min. The resulting product is a 10 wgt. % Mg/2.5 wgt % impregnated Mg-Alumina spinel ($MgAl_2O_4$). Other metals impregnated on the spinels may be synthesized in a similar manner using acetate or nitrate salts of calcium, strontium, potassium or sodium.

Catalysis Chemistry—Spinels produced from the high-temperature calcining of gamma alumina with Group II elements (Mg, Ca, Sr and Ba) have higher concentrations of basic surface hydroxy groups than gamma alumina. Furthermore, the impregnation of the metals (Ba, Ca, Co, Fe, Mg, Mn, Ni and Zn) increases the concentrations of these hydroxy groups. We have established that formates are formed when $H_2/CO_2$ mixtures react with these hydroxy groups according to Equation 1.

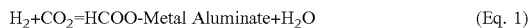

$$H_2+CO_2=HCOO\text{-Metal Aluminate}+H_2O \quad \text{(Eq. 1)}$$

These formates decompose rapidly at high temperatures in the presence of $H_2$ to primarily form CO (Equation 2).

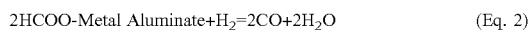

$$2HCOO\text{-Metal Aluminate}+H_2=2CO+2H_2O \quad \text{(Eq. 2)}$$

$CO_2$ Sources—Carbon capture is the process of capturing $CO_2$ from point sources. The 2-step catalytic process described herein requires that $CO_2$ feedstocks be captured efficiently and economical with minor levels of contaminants.

Several methods have been developed for the collection of $CO_2$ from one or more of the following sources: traditional air blown power plants, gasification plants, oxy-combustion power plants, cement plants, grain fermentation plants, natural gas well-heads, chemical refineries, petroleum refineries, secondary oil recovery processes and other plants that emit significant $CO_2$ emissions (Schuetzle et. al., 2010).

Power plants typically employ control devices for removing sulfur oxides and particulates. The addition of carbon capture systems requires a large additional capital cost and increased parasitic power. As a result, removal in conventional power plants can increase the cost of electricity by 50% to 70% (IGCC, 2005). The cost of capturing $CO_2$ emissions from coal power plants and natural gas power plants averages $130/ton and $95/ton, respectively (Metz et. al, 2005).

Fermentation processes are used to produce distillates (e.g., rum), wine, beer and ethanol fuels. As shown in Table 5, $CO_2$ is the primary constituent in fermentation process emissions. The concentration of ethanol is low, ranging from about 2,000-4,000 ppm. Since fermentation is an anaerobic process, $O_2$ is typically not present. Small quantities of sulfur compounds such as $H_2S$ and $SO_2$ may be present at low concentrations (Safriet, 1995).

TABLE 5

Typical Concentration of Constituents in Fermentation Process Emissions

| Constituent | Concentration |
|---|---|
| $CO_2$ | 99.6% |
| Ethanol | 3,000-4,000 ppm |
| $H_2S$ | 1.1 ppm |
| $SO_2$ | <0.2 ppm |
| $O_2$ | <0.1 ppm |

Since the concentrations of the contaminants are low, this is an ideal source of $CO_2$ for the improved direct fuel production process described in this invention. The low concentrations of sulfur compounds are easily removed using conventional adsorbents. The captured $CO_2$ cost can range from $5/ton to about $35/ton. The second catalyst in the catalytic reactor will convert most (>50 mole %) of the ethanol to liquid fuels.

The cement industry currently represents about 7% of the carbon dioxide ($CO_2$) emissions globally and is the third-largest industrial energy consumer. Cement production involves the decomposition of limestone (calcium carbonate), which represents about two-thirds of the total $CO_2$ emissions generated in the process, with the remainder of $CO_2$ emissions being due the combustion of fuels. This industry has the second-largest share of total direct industrial carbon dioxide ($CO_2$) emissions, at 27% (2.2 gigatons) of carbon dioxide per year [$GtCO_2$/yr.] in 2014 (IEA, 2018).

Cement plant emissions contain $CO_2$ at about 25 volume %. Amine (MEA) based absorption capture technology currently costs about $90/ton. If oxy-fuel is employed for heating then the cost drops to about $50/ton of $CO_2$ (Gardarsdottir et al., 2019). However, this cost can be much higher if significant cement plant modifications are required. The captured $CO_2$ from cement plants using amine capture or oxy-fuel combustion is an ideal feedstock for the production of renewable fuels from this catalytic converter and process.

Once $CO_2$ is captured it must be compressed to high pressures for storage in large vessels or cooled to produce liquid $CO_2$ which is stored in insulated containers. Therefore, if the captured $CO_2$ is directly converted to liquid fuels at the plant site, these costs are eliminated.

Several technologies have been developed to collect $CO_2$ from ambient air (U.S. Pat. No. 9,095,813 B2). The challenges with these ambient air collection processes is that the cost of $CO_2$ collection is very high, with current costs ranging from $400-600/metric ton or higher, however costs may decline as these technologies are commercialized.

There are some $CO_2$ sources that are associated with significant levels of $C_1$-$C_6$ hydrocarbons. Some examples of such sources include $CO_2$/light hydrocarbon mixtures from natural gas well heads, emissions from secondary oil recovery using $CO_2$ and biogas.

Injection of CO$_2$ into oil reservoirs is a common method of secondary oil recovery. After CO$_2$ injection, the recovered CO$_2$ contains light hydrocarbons which need to be separated before CO$_2$ re-injection. U.S. Pat. No. 9,159,105 describes a process for separating the light hydrocarbons from CO$_2$ using an air capture unit. The CO$_2$ is re-injected into the well for additional oil recovery and the light hydrocarbons are used as a fuel for local use.

Various Embodiments

Processes
1. A process for the conversion of carbon dioxide into a liquid fuel, wherein the process comprises the steps of:
   a) introducing a gaseous mixture of carbon dioxide and hydrogen, or a mixture of carbon dioxide, hydrogen and light hydrocarbons into a first catalytic reactor in a catalytic conversion system to produce syngas, wherein the first catalyst in the catalytic conversion system is produced from the impregnation of magnesium aluminate, calcium aluminate, strontium aluminate, potassium aluminate or sodium aluminate spinels with up to 35 wt. % (e.g., 1 part-by-weight to 35 parts-by weight, 5 parts-by-weight to 35 parts-by-weight or 10 parts-by weight to 35 parts-by weight) of one or more of the following elements (Ba, Ca, Co, Fe, Mg, Mn, Ni and Zn) followed by calcining of the impregnated spinel up to 2,150° F.
   b) introducing the syngas into a second catalytic reactor in the catalytic conversion system to produce tailgas, water and liquid fuel, wherein the second catalyst comprises about 2 to about 35 parts-by-weight (e.g., 3 to 35 parts-by-weight, 5 to 35 parts-by-weight or 10 to 35 parts-by-weight) of an element wherein the element is selected from a group of elements consisting of cobalt, iron, magnesium, manganese, calcium, barium, copper and zinc, and from about 0.1 to about 5 parts-by-weight (e.g. 0.2 to 5 parts-by-weight, 1 to 5 parts-by-weight or 2 to 5 parts-by-weight) of at least one metal selected from a group consisting of cerium, ruthenium, lanthanum, platinum, or rhenium per 100 parts-by-weight of a support selected from a group consisting of silica, alumina, and combinations thereof thereby producing liquid fuel, tailgas and water; c) separating the liquid fuel, tailgas and water from one another thereby producing the liquid fuel.
2. The process according to Processes "1" above, wherein the CO$_2$ introduced into the first catalytic reactor is obtained from a source, wherein the source is selected from a group of sources including traditional air blown power plants, gasification plants, oxy-combustion power plants, cement plants, grain fermentation plants, natural gas well-heads, chemical refineries, petroleum refineries, secondary oil recovery processes and other plants that produce CO$_2$ emissions. In addition, the CO$_2$ may be obtained from direct air capture systems.
3. The process according to Processes "1" above, wherein the hydrogen is generated using electrolysis, wherein the power for the electrolysis is generated from a renewable or low-carbon source, and wherein the renewable or low carbon source is selected from a group of sources consisting of wind, solar, geothermal, hydro, ocean currents, biomass, flare gas, nuclear, off-peak power from a fossil fuel plant, and power produced by an oxy-combustion plant.
4. The process according to Processes "1" above, wherein the tailgas is recycled back to the catalytic conversion system.
5. The process according to Processes "1" above, wherein the water is used for greywater applications.
6. The process according to Processes "1" above, wherein the second catalytic reactor is operated at a pressure from about 150 psi to about 400 psi (e.g., 150 psi to 400 psi) or preferably from about 250 psi to about 350 psi (e.g., 250 psi to 350 psi).
7. The process according to Processes "1" above, wherein the tailgas is partially combusted with oxygen from an electrolysis system used to generate the hydrogen to produce syngas and heat, and wherein the syngas is mixed with the other gases introduced into the second catalytic reactor.
8. The process according to Processes "1" above, wherein the liquid fuel is used without further processing as fuel for off-road diesel engines.
9. The process according to Processes "1" above, wherein the liquid fuel is blended with petroleum diesel fuel to provide a fuel blend.
10. The process according to Processes "1" above, wherein the liquid fuel is distilled to provide #1 diesel, #2 diesel, #3 diesel and/or jet fuel.

Catalysts
1. A catalyst for the conversion of carbon dioxide into syngas, wherein the first catalyst is synthesized by a process comprising the impregnation of magnesium aluminate, calcium aluminate, strontium aluminate, potassium aluminate or sodium aluminate spinels with up to 35 wt. % of one or more of the following elements (Ba, Ca, Co, Fe, Mg, Mn, Ni and Zn) followed by calcining of the impregnated spinel up to 2,150° F.
2. A first catalyst, wherein the first catalyst comprises magnesium aluminate spinel impregnated with between 5 wt. % and 35 wt. % Ba, Ca or Co.
3. A first catalyst, wherein the first catalyst comprises magnesium aluminate spinel impregnated with between 5 wt. % and 35 wt. % Fe, Mg or Mn.
4. A first catalyst, wherein the first catalyst comprises magnesium aluminate spinel impregnated with between 5 wt. % and 35 wt. % Ni or Zn.
5. A first catalyst, wherein the first catalyst comprises calcium aluminate spinel impregnated with between 5 wt. % and 35 wt. % Ba, Ca or Co.
6. A first catalyst, wherein the first catalyst comprises calcium aluminate spinel impregnated with between 5 wt. % and 35 wt. % Fe, Mg or Mn.
7. A first catalyst, wherein the first catalyst comprises calcium aluminate spinel impregnated with between 5 wt. % and 35 wt. % Ni or Zn.
8. A first catalyst, wherein the first catalyst comprises strontium aluminate spinel impregnated with between 5 wt. % and 35 wt. % Ba, Ca or Co.
9. A first catalyst, wherein the first catalyst comprises strontium aluminate spinel impregnated with between 5 wt. % and 35 wt. % Fe, Mg or Mn.
10. A first catalyst, wherein the first catalyst comprises strontium aluminate spinel impregnated with between 5 wt. % and 35 wt. % Ni or Zn.
11. A first catalyst, wherein the first catalyst comprises potassium aluminate spinel impregnated with between 5 wt. % and 35 wt. % Ba, Ca or Co.
12. A first catalyst, wherein the first catalyst comprises potassium aluminate spinel impregnated with between 5 wt. % and 35 wt. % Fe, Mg or Mn.

13. A first catalyst, wherein the first catalyst comprises potassium aluminate spinel impregnated with between 5 wt. % and 35 wt. % Ni or Zn.

14. A first catalyst, wherein the first catalyst comprises sodium aluminate spinel impregnated with between 5 wt. % and 35 wt. % Ba, Ca or Co.

15. A first catalyst, wherein the first catalyst comprises sodium aluminate spinel impregnated with between 5 wt. % and 35 wt. % Fe, Mg or Mn.

16. A first catalyst, wherein the first catalyst comprises sodium aluminate spinel impregnated with between 5 wt. % and 35 wt. % Ni or Zn.

17. A second catalyst, wherein the second catalyst comprises 2 to 25 parts-by-weight of cobalt and 0.1 to 5 parts-by-weight of cerium, ruthenium, lanthanum, platinum, rhenium or combinations thereof per 100 parts-by-weight of a support.

18. A second catalyst, wherein the second catalyst comprises 2 to 25 parts-by-weight of iron and 0.1 to 5 parts-by-weight of cerium, ruthenium, lanthanum, platinum, rhenium or combinations thereof per 100 parts-by-weight of a support.

19. A second catalyst, wherein the second catalyst comprises 2 to 25 parts-by-weight of magnesium and 0.1 to 5 parts-by-weight of cerium, ruthenium, lanthanum, platinum, rhenium or combinations thereof per 100 parts-by-weight of a support.

20. A second catalyst, wherein the second catalyst comprises 2 to 25 parts-by-weight of manganese and 0.1 to 5 parts-by-weight of cerium, ruthenium, lanthanum, platinum, rhenium or combinations thereof per 100 parts-by-weight of a support.

21. A second catalyst, wherein the second catalyst comprises 2 to 25 parts-by-weight of calcium and 0.1 to 5 parts-by-weight of cerium, ruthenium, lanthanum, platinum, rhenium or combinations thereof per 100 parts-by-weight of a support.

22. A second catalyst, wherein the second catalyst comprises 2 to 25 parts-by-weight of barium and 0.1 to 5 parts-by-weight of cerium, ruthenium, lanthanum, platinum, rhenium or combinations thereof per 100 parts-by-weight of a support.

23. A second catalyst, wherein the second catalyst comprises 2 to 25 parts-by-weight of copper and 0.1 to 5 parts-by-weight of cerium, ruthenium, lanthanum, platinum, rhenium or combinations thereof per 100 parts-by-weight of a support.

24. A second catalyst, wherein the second catalyst comprises 2 to 25 parts-by-weight of zinc and 0.1 to 5 parts-by-weight of cerium, ruthenium, lanthanum, platinum, rhenium or combinations thereof per 100 parts-by-weight of a support.

Catalytic Reactors

1. A catalytic conversion system for the conversion of carbon dioxide into a liquid fuel, wherein the catalytic system comprises a first catalytic reactor and a second catalytic reactor, wherein the first catalytic reactor comprises a first catalyst and second catalyst in series, the composition of which have been previously described above.

2. The catalytic conversion system according to Catalytic Reactors "1" above, wherein the catalytic conversion system further comprises a heat exchanger between the first catalytic reactor and the second catalytic reactor, wherein gas flows from the first catalytic reactor to the heat exchanger and then to the second catalytic reactor.

3. The catalytic conversion system according to Catalytic Reactors "1" above, wherein the catalytic conversion system further comprises a gas blending chamber that is connected to the first catalytic reactor such that gas can flow between the gas blending chamber to the first catalytic reactor.

4. The catalytic conversion system according to Catalytic Reactors "1" above, wherein the catalytic conversion system further comprises an electrolysis system for the production of hydrogen, wherein the electrolysis system is connected to the gas blending chamber such that hydrogen produced can flow to the gas blending chamber.

5. The catalytic conversion system according to Catalytic Reactors "3" above, wherein the catalytic conversion system further comprises a system for capturing carbon dioxide, wherein the system for capturing carbon dioxide is connected to the gas blending chamber such that carbon dioxide obtained in the carbon dioxide capturing system can flow to the gas blending system.

6. The catalytic conversion system according to Catalytic Reactors "4" above, wherein the catalytic conversion system further comprises a system for capturing carbon dioxide, wherein the system for capturing carbon dioxide is connected to the gas blending chamber such that carbon dioxide obtained in the carbon dioxide capturing system can flow to the gas blending system.

Further Processes and Catalysts

1. A process that efficiently converts $CO_2/H_2$ mixtures, or mixtures of $CO_2/H_2$ and light hydrocarbons, directly into synthetic liquid fuels by employing a catalytic process which contains two catalysts wherein the first catalyst in the catalytic conversion system is synthesized from the impregnation of one or more of the following elements (Ba, Ca, Co, Fe, Mg, Mn, Ni and Zn) on a metal-alumina spinel consisting of magnesium aluminate, calcium aluminate, strontium aluminate, potassium aluminate or sodium aluminate up to a concentration of about 35 parts-by-weight (e.g., 1 part-by-weight to 35 parts-by weight, 5 parts-by-weight to 35 parts-by-weight or 10 parts-by weight to 35 parts-by weight) and calcining of the impregnated spinel up to 2,150° F. (e.g., 1,000° F. to 2,150° F., 1,500° F. to 2,150° F., or 1,750° F. to 2,150° F.) are efficient for the production of syngas from mixtures of $CO_2$ and $H_2$.

2. The process according to Further Processes and Catalysts "1" above in which $H_2$ is produced from water using electrolysis.

3. The process according to Further Processes and Catalysts "1" above in which $H_2$ may be produced from the steam reforming of solid carbonaceous substances such as biomass, flare gas, biogas, methane, light hydrocarbons and other constituents that contain various stoichiometric mixtures of carbon, hydrogen and oxygen.

4. The process according to Further Processes and Catalysts "1" above in which the $CO_2$ introduced into the first catalytic reactor is collected from a one or more of the following sources: traditional air blown power plants, gasification plants, oxy-combustion power plants, cement plants, grain fermentation plants, natural gas well-heads, chemical refineries, petroleum refineries, secondary oil recovery processes and other plants that emit significant $CO_2$ emissions.

5. The process according to Further Processes and Catalysts "1" above in which the ratios of the $H_2/CO_2$ mixture input into the catalytic conversion process may vary from 1.5/1.0 to 4.0/1.0, and preferably from 2.0/1.0 to 3.5/1.0.

6. The process according to Further Processes and Catalysts "1" above in which the $H_2/CO_2$ mixture is input into the catalytic converter at pressures between 150 and 350 psi.

7. The process according to Further Processes and Catalysts "1" above in which the $H_2/CO_2$ mixture is heated to a temperature that is greater than the operating temperature of the first catalyst so that the first catalyst requires little or no additional heating.

8. The first catalyst according to Further Processes and Catalysts "1" above which may be used in tubular fixed bed reactors, fluidized bed reactors, moving bed reactors, rotating bed reactors, slurry bed reactors and other reactors commonly used in the art.

9. The first catalyst according to Further Processes and Catalysts "1" above which is reduced at temperatures up to about 1,200° F.

10. The reduced catalyst according to Further Processes and Catalysts "1" above which efficiently converts mixtures of $H_2$ and $CO_2$ to syngas when the catalyst is operated at pressures in the range of 100-350 psi and more preferably in the range of 150-300 psi.

11. The catalyst according to Further Processes and Catalysts "1" above which efficiently converts mixtures of $H_2$ and $CO_2$ to syngas when the catalyst is operated above 2,500 $hr^{-1}$ space velocity's (e.g., 2,500 $hr^{-1}$ to 40,000 $hr^{-1}$).

12. The catalyst according to Further Processes and Catalysts "1" above which efficiency converts mixtures of $H_2$ and $CO_2$ to syngas in which the $H_2$ to $CO_2$ ratio may vary from 1.0 to 4.0 and preferably from 1.5 to 3.5.

13. The catalyst according to Further Processes and Catalysts "1" above in which syngas is produced with a $CO_2$ to CO conversion efficiency of greater than about 65% (e.g., 65% to 100%) at 1,650° F. at 150-300 psi pressures.

15. The catalyst according to Further Processes and Catalysts "1" above which produces syngas with an $H_2$/CO ratio in the range of 1.0-3.0 and preferably 1.5-2.5.

16. The catalyst according to Further Processes and Catalysts "1" above which has a thermal stability up to 2,100° F. (e.g. at 2,100° F.).

17. The catalyst according to Further Processes and Catalysts "1" above which is resistant to contaminants present in captured $CO_2$ streams, natural gas, biogas or other gas feedstock streams.

18. The catalyst according to Further Processes and Catalysts "1" above in which the catalyst forms no or nominal carbon via coking.

19. The catalyst according to Further Processes and Catalysts "1" above in which $CH_4$, when present in the $CO_2$/$H_2$ mixture, is efficiently converted to syngas.

20. The catalyst according to Further Processes and Catalysts "1" above in which $C_2$-$C_7$ hydrocarbons, when present in the $CO_2$/$H_2$ mixture, are efficiently converted to syngas.

21. The process according to Further Processes and Catalysts "1" above which efficiently produces syngas when 02 is added to the selected mixtures of $CO_2$, $H_2$, $CH_4$, and $C_2$-$C_5$ hydrocarbons.

22. The process according to Further Processes and Catalysts "1" above in which the syngas is feed into other catalytic reactors to produce fuels and/or chemicals.

23. The process according to Further Processes and Catalysts "1" above in which a heat exchanger is used to reduce the temperature from the first catalyst to the operating temperature of the second catalyst to 400-475° F.

24. The process according to Further Processes and Catalysts "1" above in which the cooled syngas is feed into a second catalyst, and wherein this second catalyst comprises from about 2 to about 25 parts-by-weight cobalt (e.g., 2 to 25 parts-by-weight) and from about 0.1 to about 10 parts-by-weight (e.g., 0.1 to 10 parts-by weight) of at least one metal selected from a group consisting of cerium, ruthenium, lanthanum, platinum, palladium, and rhenium per 100 parts-by-weight of a support selected from a group consisting of silica, alumina, and combinations thereof; thereby producing a diesel fuel.

25. The process according to Further Processes and Catalysts "1" above in which the second catalyst produces $C_1$-$C_5$ gas-phase hydrocarbons; $C_5$-$C_{23}$ liquid phase hydrocarbons; a tail-gas consisting of CO, $H_2$, $C_1$-$C_5$ hydrocarbons, $CO_2$ and $H_2O$; and $C_{24}$+ hydrocarbons.

26. The process according to Further Processes and Catalysts "25" above comprising introducing the product stream from the second reactor and catalyst system into a separator that separates the $C_{24}$+ hydrocarbons from the other products.

27. The process according to Further Processes and Catalysts "25" above in which the partitioning of the $C_{24}$+ hydrocarbons from the $C_5$-$C_{23}$ hydrocarbons is controlled by varying the separator temperature.

28. The process according to Further Processes and Catalysts "25" above in which the remaining liquid product stream is condensed into two fractions wherein the top fraction contains the liquid hydrocarbon fuel and the bottom fraction comprises water.

29. The process according to Further Processes and Catalysts "25" above in which the liquid hydrocarbon fuel is separated from the water.

30. The process according to Further Processes and Catalysts "29" above in which the liquid hydrocarbon fuel is used directly for off-road diesel engines and vehicles.

31. The process according to Further Processes and Catalysts "29" above in which the liquid hydrocarbon fuel is blended with petroleum diesel fuel and used for on-road diesel engines and vehicles.

32. The process according to Further Processes and Catalysts "29" above in which the synthetic liquid fuel is distilled to produce diesel fuel #1; diesel fuel #2; jet fuel; reformulated gasoline blendstocks; and a minor fraction (less than about 5 volume %) of heavy ($C_{24}$+) hydrocarbons.

33. The process according to Further Processes and Catalysts "29" above in which the reformulated gasoline blendstock is blended with petroleum gasoline fuels and used for spark-ignition engines and vehicles.

34. The process according to Further Processes and Catalysts "29" above in which the diesel #1 (kerosene) is used for kerosene heaters and stoves.

35. The process according to Further Processes and Catalysts "29" above in which the diesel #1 (kerosene) is used for jet engines and turbines.

36. The process according to Further Processes and Catalysts "29" above in which the neat or blended synthetic fuels reduce criteria engine emissions by at least 2% compared to petroleum based fuels.

37. The process according to Further Processes and Catalysts "29" above in which the neat or blended synthetic fuels improve one or more fuel properties by at least 2% compared to petroleum based fuels.

38. The process according to Further Processes and Catalysts "29" above in which the neat or blended synthetic fuels reduce greenhouse gas emissions by at least 2% compared to petroleum based fuels.

39. The process according to Further Processes and Catalysts "29" above in which specific normal aliphatic hydrocarbons in the liquid hydrocarbon fuel product are separated using distillation and/or adsorbents.

40. The process according to Further Processes and Catalysts "29" above in which specific normal 1-alkenes in the liquid hydrocarbon fuel product are separated using distillation and/or adsorbents.

41. The process according to Further Processes and Catalysts "29" above in which specific normal 1-hydroxyalkanes in the liquid hydrocarbon fuel product are separated using distillation and/or adsorbents.

42. The processes according to Further Processes and Catalysts "39"-"41" above wherein the separated, specific normal aliphatic hydrocarbons, normal 1-alkenes, and normal 1-alkenes are produced that have a purity of at least 95%, more preferably 98%, and even more preferably 99%.

43. The process according to Further Processes and Catalysts "40" above in which the $C_5$-$C_{16}$ normal 1-alkenes in the liquid hydrocarbon fuel product are converted to normal 1-hydroxyalkanes by catalytic hydration.

44. The process according to Further Processes and Catalysts "41" above in which the normal 1-hydroxyalkanes in the liquid hydrocarbon fuel product are converted to normal 1-alkenes by catalytic de-hydration.

45. The process according to Further Processes and Catalysts "40" above in which $C_5$-$C_{16}$ normal 1-alkenes in the liquid hydrocarbon fuel product is converted to synthetic lubricants by catalytic oligomerization.

46. The process according to according to Further Processes and Catalysts "29" above in which some of the tailgas is recycled back to catalyst #2 for the production of additional products.

47. The process according to according to Further Processes and Catalysts "29" above in which some of the tailgas is converted to additional syngas by partial oxidation with oxygen (e.g. ATR conversion) or by autothermal reforming (ATR) produced from electrolysis.

48. The process according to Further Processes and Catalysts "40" above in which the heated syngas is added to the $H_2/CO_2$ stream before input into the first catalyst.

49. The process according to Further Processes and Catalysts "40" above in which the syngas is feed into other types of catalytic processes to produce fuels and/or chemicals.

50. The process according to Further Processes and Catalysts "40" above in which the syngas is used to produce power using gen-sets, gas-turbines and other established gas to power equipment.

51. The process according to Further Processes and Catalysts "40" above in which the syngas is used as a burner fuel for the production of heat.

52. The process according to Further Processes and Catalysts "40" above in which the second catalyst is used for the production of ammonia.

53. The process of Further Processes and Catalysts "1" in which the second catalyst is a Fischer Tropsch (F-T) type catalyst formulation that produces wax, followed by the conversion of that wax into fuels and/or chemicals using conventional wax hydro-reforming and hydro-processing methods.

54. The process of Further Processes and Catalysts "1" in which the second catalyst produces methanol, ethanol and/or other alcohols.

55. The process of Further Processes and Catalysts "1" in which the second catalyst is used for the production of methanol, the methanol which is then converted into gasoline using additional, conventional catalysts and processes described in the current art.

| U.S. patent application Documents | | |
|---|---|---|
| 2003/0113244 AI | June 2003 | DuPont et al |
| 2005/0166447 AI | August 2005 | Corkwell et al |
| 2006/0144755 AI | July 2006 | Benazzi et al |
| 2008/0108716 AI | May 2008 | Ayasse |
| 2009/0300970 AI | December 2009 | Perego et al |
| 2010/0160463 AI | June 2010 | Wang et al |
| 2012/0208902 AI | August 2012 | Kresnyak et al |
| 2017/0321333 A1 | November 2017 | Kuhl et al |

| U.S. Pat. Documents | | |
|---|---|---|
| 4,990,491 A | June 1988 | Wagner et al |
| 6,402,989 B1 | June 2002 | Gaffney et al |
| 6,423,665 B1 | July 2002 | Okado et al |
| 6,946,114 B2 | September 2005 | Allison et al |
| 7,432,222 B2 | October 2008 | Choudhary et al |
| 7,718,832 B1 | May 2010 | Schuetzle et al |
| 8,198,338 B1 | xx/2012 | Schulenberger et al |
| 8,394,862 B1 | March 2013 | Schuetzle et al |
| 8,741,001 B1 | June 2014 | Schuetzle et al |
| 9,090,831 B2 | July 2015 | Schuetzle et al |
| 9,095,813 B2 | September 2015 | Keith et al |
| 9,476,002 B1 | October 2016 | Schuetzle et al |
| 9,611,145 B1 | April 2017 | Schuetzle et al |
| 9,631,147 B1 | April 2017 | Schuetzle et al |
| 10,478,806 B1 | November 2019 | Schuetzle et al |

| Foreign Patent Documents | | |
|---|---|---|
| AU 2015/203898 B2 | July 2015 | Landau et al |
| GB 1995/2279583 A | 11/995 | Iwanani et al |

OTHER PUBLICATIONS

Allam, R., Palmer, M. R., Brown, W., Fetvedta, J., Freeda, D., Nomoto, H., Itoh, M., Okita, N., Jones, C.: High efficiency and low cost of electricity generation from fossil fuels while eliminating atmospheric emissions, including carbon dioxide, Energy Procedia 37, 1135-1149 (2013) (DOI: 10.1016/j.egypro.2017.03.1731).

Allam, R., Martin, S., Forrest, B., Fetvedt, J., Lu, X., Freed, D., Brown, W., Sasaki, T., Itoh, M., Manning, J.: Demonstration of the Allam cycle: an update on the development status of a high efficiency supercritical carbon dioxide power process employing full carbon capture, Energy Procedia 114, 5949-5966 (2017) (DOI: 10.1016/j.egypro.2017.03.1731).

Arakawa, H.: Catalysis research of relevance to carbon management: progress, challenges, and opportunities. Chem. Rev. 101, 953-996 (2001) (DOI: 10.1021/cr000018s).

Artz, J., Müller, T. E., Thenert, K., Kleinekorte, J., Meys, R., Sternberg, A., Bardow, A, Leitner, W: Sustainable conversion of carbon dioxide: An integrated review of catalysis and life cycle assessment. Chemical Reviews, 118, 434-504 (2018).

Ashcroft, A. T., Cheetham, A. K., Green, M. L. H., and Vernon, P. D. F.: Partial oxidation of methane to synthesis gas using carbon dioxide, Nature, 352, 255-256 (1991).

Bahmanpour, A. M., Heroguel, F., Kilic, M., Baranowski, C. J., Artiglia, L.: Cu—Al spinel as a highly active and catalyst for the reverse water gas shift reaction. ACS Catal., 9, 6243-6251 (2019).

Centi, G., Perathoner, S.: Opportunities and prospects in the chemical recycling of carbon dioxide to fuels. Catalysis Today 148, 191-205 (2009) (DOI: 10.1016/j.cattod.2009.07.075).

Chen, P., Zhao, Guofeng, Z., Xue-Rong, J., Zhu, J. D., Lu, Y.: Catalytic technology for carbon dioxide reforming of methane to syngas. iScience 17, 315-324 (2019) (DOI: 10.1016/j.isci.2019.07.006.

Choudhary, V. R., Dajput, A. M., and Brabhapar, B.: Energy efficient methane-to-syngas conversion with low H2/CO ratio by simultaneous catalytic reactions of methane, Catalysis Letters, 32, 391-396 (1995).

Daza, Y. A., Kuhn, J. N.: $CO_2$ conversion by reverse water gas shift catalysis: Comparison of catalysts, mechanisms and their consequences for $CO_2$ conversion to liquid fuels, Royal Society of Chemistry Advances, 1-31 (2016) (DOI: 10.1039/C6RA05414E).

Fischer, N., Claeys, M., Van Steen, E., Niemantsverdriet, H., Vosloo, M.: Syngas convention—fuels and chemicals from synthesis gas: state of the art 2, 1-200 (2016).

Fulkerson, W., Judkins, R. R., Sanghvi, M. K.: Energy from fossil fuels, Scientific American, 263, 128-135 (1990) (DOI: 10.1038/scientificamerican0990-128).

Hill, M. R.: How to make renewable natural gas, 2018, 2018 AGA-EPA RNG Workshop (Oct. 23, 2018).

Intergovernmental Panel on Climate Change: IPCC special report on $CO_2$ capture and storage, Cambridge University Press, Cambridge (2005).

Jafari, M., Sadaf, A., Behroozarand, A., Ghasemzadeh, K., Wood, D. A.: Plant-wide simulation of an integrated zero-emission process to convert flare gas to gasoline, Gas Processing Journal, 6, 1-20 (2018) (DOI: 10.22108/gpj.2018.111048.1028).

Jiang, Z., Xiao, T., Kuznetsov, V. L., Edwards, P. P.: Turning carbon dioxide into fuel. Phil. Trans. R. Soc. A, 368, 3343-3364 (2010) (DOI: 10.1098/rsta.2010.0119).

Kothandaraman, J., Goeppert, A., Czaun, M., Olah, G. A., Prakash, G. K. S.: Conversion of $CO_2$ from air into methanol using a polyamine and a homogeneous ruthenium catalyst J. Am. Chem. Soc. 138, 778-781 (2016) (DOI:10.1021/jacs.5b12354).

Li, W., Wang, H., Jiang, X., Zhu, J., Liu, Z., Guo, X., Song, C.: A short review of recent advances in $CO_2$ hydrogenation to hydrocarbons over heterogeneous catalysts, RSC Adv., 8, 7651 (2018) (DOI: 10.1039/c7ra13546g).

Lortie, M.: Reverse water gas shift reaction over supported Cu—Ni nanoparticle catalysts, Department of Chemical and Biological Engineering M.S. Thesis, University of Ottawa, Ottawa, Canada (2014).

Marti, C., Pacifici, L., Capriccioli, A., Lagana, A.: Simulation of methane production from carbon dioxide on a collaborative research infrastructure, International Conference on Computational Science and Its Applications ICCSA 2016: Computational Science and Its Applications—ICCSA, 319-333 (2016).

Melaina, M. W., Antonia, O., Penev, M.: Blending hydrogen into natural gas pipeline networks: a review of key issues. National Renewable Energy Laboratory, Technical Report #5600-51995 (2013).

Messias, S., Sousa, M. M., daPonte, M. N., Rangel, C. M., Pardal, T., Machado, A. S. R.: Electro-chemical production of syngas from $CO_2$ at pressures up to 30 bars in electrolytes containing ionic liquid, React. Chem. Eng., 4, 1982-1990 (2019).

Metz, B., Davidson, O., de Connick, H. C., Loos, M., Meyer, L. A.: IPCC special report on carbon dioxide capture and storage, Intergovernmental Panel on Climate Change, Cambridge University Press, Cambridge, United Kingdom and New York, N.Y., USA, 442 pages (2005).

Mikkelsen, M., Jorgensen, M., Krebs, F. C.: The teraton challenge—a review of fixation and transformation of carbon dioxide. Energy Environ. Sci. 3, 43-81 (2010) (DOI: 10.1039/b912904a).

National Academy of Sciences, Chemical Utilization of $CO_2$ into Chemicals and Fuels, Gaseous Carbon Waste Streams Utilization: Status and Research Needs, National Academies Press, Washington D.C. (2019) (DOI: 10.17226/25232).

Olah, G. A.: Beyond oil and gas: the methanol economy. Angew. Chem. Int. Edn. 44, 2636-2639 (2005) (DOI: 10.1002/anie.200462121).

Olah, G. A., Goeppert, A., Surya Prakash, G. K.: Chemical recycling of carbon dioxide to methanol and dimethyl ether—from greenhouse gas to renewable, environmentally carbon neutral fuels and synthetic hydrocarbons. J. Org. Chem. 74, 487-498 (2009) (DOI: 10.1021/jo801260f).

Owen, R. E., Mattia, D., Plucinski, P., Jones, M. D., Kinetics of $CO_2$ hydrogenation to hydrocarbons over Iron-Silica catalysts, Physical Chemistry, 18, 3211-3218 (2017).

Pan, X., Fan, Z., Chen, W., Ding, Y., Luo, H. & Bao, X.: Enhanced ethanol production inside carbon-nanotube reactors containing catalytic particles, Nat. Mater. 6, 507-511 (2007) (DOI: 10.1038/nmat1916).

Pearson, R. J., Turner, J. W. G., Peck, A. J.: Gasoline-ethanol-methanol tri-fuel vehicle development and its role in expediting sustainable organic fuels for transport. *Low carbon vehicles*, Institute of Mechanical Engineers Conference, London, May 2009 (2009) (www.grouplotus.com/mediagallery/image/1002548.pdf).

Ruckenstein, E., Hu, Y. H.: Combination of CO2 reforming and partial oxidation of methane over NiO/MgO Solid Solution, Industrial & Engineering Chemistry Research, 37, 1744-1747 (1998).

Sakakura, T., Choi, J.-C., Yasuda, H.: Transformation of carbon dioxide. Chem. Rev. 107, 2365-2387 (2007) (DOI: 10.1021/cr068357u).

Senderens, J.-B., Sabatier, P.: Nouvelles syntheses du methane. Comptes Rendus Acad. Sci. 82, 514-516 (1902).

Safriet, D.: Emission factor documentation for AP-12, Section 9.12.2 Wines and Brandy, U.S. EPA, Office of Air Quality Planning and Standards, Research Triangle Park, N.C. (October 1995).

Semelsberger, T. A., Borup, R. L., Greene, H. L.: Dimethyl Ether (DME) as an alternative fuel, Journal of Power Sources 156, 497-511 (2006).

SoCalGas, Renewable natural gas (RNG) gas quality standards (www.socalgas.com/rg) (2019).

Schuetzle, D., Tamblyn, G., Caldwell, M., Schuetzle, R.: Solar reforming of carbon dioxide to produce diesel fuel. DOE report #DE-FE0002558 (2010).

Schuetzle, D.: Historical and predicted global climate changes and some potential accelerated climate moderation approaches, 2018 Global Climate Action Summit, San Francisco, Calif., 1-42 (Sep. 10-14, 2018); Research Gate (www.researchgate.net) (Apr. 24, 2017 and Jan. 26, 2020 update).

Vogt, C., Monai, M., Kramer, G. J., Weckhuysen, B. M.: The renaissance of the Sabatier reaction and its applications on Earth and in space, Nature Catalysis, 2, 188-197 (2019).

Wang, W., Wang, S., Ma, X, Gong, J.: Recent advances in catalytic hydrogenation of carbon dioxide, Chem. Soc. Rev, 40, 3703-3727 (2011) (DOI: 10.1039/c1cs15008a).

Wang, Y., Liu, T., Lei, L., Chen, F.: High temperature solid oxide $H_2O/CO_2$ co-electrolysis for syngas production, Fuel Processing Technology, 161 (2016) (10.1016/j.fuproc.2016.08.009).

Wang, T., Stiegel, G.: Integrated gasification combined cycle (IGCC) technologies, Elsevier, Oxford, U.K. (2017).

Williamson, D., Herdes, C., Torrente-Murciano, L., Jones, M., Mattia, D.: N-doped Fe for combined RWGS-FT $CO_2$ hydrogenation, 7, 7395-7402, ACS Sustainable Chem. Engineering (2019).

Wiectaw-Solny, L., Tararczuk, A., Krótki, A., Stec, M.: The technological research progress of amine-based $CO_2$ capture, Polityka Energ. 16, 229-240 (2013). Wikipedia: Energy density (2013) (www.en.wikipedia.org/wiki-/Energy_density).

Zaki, T., Sakr, A., Natural gas origin, composition and processing: a review, Journal of Natural Gas Science and Engineering 34 (2016); DOI: 10.1016/j.jngse.2016.06.030.

Zhang, J., Wang, H., and Dalai, A. K., Development of stable bimetallic catalysts for carbon dioxide reforming of methane. Journal of Catalysis, 249, 300-310 (2007).

Zhou, Z., Ersoy, D.: Review studies of hydrogen use in natural gas distribution systems, Gas Technology Institute, Chicago, Ill., National Renewable Energy Laboratory, Technical Report #21029 (2010).

Zhu, Q.: Developments on $CO_2$-utilization technologies, Clean Energy, 3, 85-100 (2019) (DOI: 10.1093/ce/zkz008).

What is claimed is:

1. A process for the conversion of power and carbon dioxide into a liquid fuel, wherein the process comprises the steps of:
   a) producing hydrogen and oxygen from the electrolysis of water;
   b) introducing the hydrogen in combination with carbon dioxide into a first catalytic reactor that comprises a first $CO_2$ hydrogenation catalyst that produces syngas;
   c) introducing the syngas into a second catalytic reactor that uses a second catalyst that primarily produces liquid fuel and tailgas;
   d) introducing the tailgas from the second catalytic reactor to a tailgas conversion system that utilizes oxygen from the electrolyzer to produce additional syngas
   wherein the first $CO_2$ hydrogenation catalyst comprises a metal alumina spinel impregnated with a second element at a concentration between 1 part-by-weight and 35 parts-by-weight, and wherein the metal alumina spinel is selected from a group consisting of magnesium aluminate, calcium aluminate, strontium aluminate, potassium aluminate and sodium aluminate, and wherein the second element is selected from a group consisting of Ba, Ca, Co, Fe, Mg, Ni and Zn;
   and wherein the first catalytic reactor is operated at a temperature from 1.500 to 2.000° F.;
   and wherein there is a conversion efficiency of CO2 to CO for the process, and wherein the conversion efficiency is 65 percent to 100 percent.

2. The process according to claim 1, wherein hydrogen is generated using electrolysis, and wherein the power for the electrolysis is generated from a renewable or low-carbon source, and wherein the renewable or low carbon source is selected from a group of sources consisting of wind, solar, geothermal, hydro, ocean currents, biomass, flare gas, nuclear, and power produced by an oxy-combustion plant.

3. The process according to claim 1, wherein the $CO_2$ introduced into the first catalytic reactor is collected from a one or more of the following sources:
   traditional air blown power plants, gasification plants, oxy-combustion power plants, cement plants, grain fermentation plants, natural gas well-heads, chemical refineries, petroleum refineries, secondary oil recovery processes and other plants that emit significant $CO_2$ emissions.

4. The process according to claim 1, wherein the first catalytic reactor is operated at a pressure from 150 psi to 350 psi.

5. The process according to claim 1, wherein the tailgas conversion system is partial oxidation.

6. The process according to claim 1, wherein the tailgas conversion system is authothermal reforming (ATR).

7. The process according to claim 1, wherein the syngas is introduced into a heat exchanger to reduce the temperature of the syngas before it is introduced into the second catalytic reactor.

8. The process according to claim 1, wherein the second catalytic reactor is operated at a pressure from 150 psi to 350 psi.

* * * * *